United States Patent
Guerra et al.

(10) Patent No.: US 8,485,194 B2
(45) Date of Patent: *Jul. 16, 2013

(54) ORAL AIRWAY

(76) Inventors: Phillip Benjamin Guerra, Arlington, TX (US); Paul R. Prince, San Juan Capistrano, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/550,666

(22) Filed: Jul. 17, 2012

(65) Prior Publication Data

US 2013/0014754 A1   Jan. 17, 2013

Related U.S. Application Data

(63) Continuation of application No. 13/168,948, filed on Jun. 25, 2011, now Pat. No. 8,220,461.

(60) Provisional application No. 61/438,465, filed on Feb. 1, 2011.

(51) Int. Cl.
*A61M 11/00* (2006.01)
(52) U.S. Cl.
USPC ................................ 128/207.14; 128/200.26
(58) Field of Classification Search
None
See application file for complete search history.

(56) References Cited

U.S. PATENT DOCUMENTS

| | | |
|---|---|---|
| 3,756,244 A | 9/1973 | Kinnear et al. |
| 4,669,463 A | 6/1987 | McConnell |
| 4,739,756 A | 4/1988 | Horn |
| 4,821,714 A | 4/1989 | Smelser |
| 4,977,894 A | 12/1990 | Davies |
| 5,413,095 A | 5/1995 | Weaver |
| 5,513,634 A | 5/1996 | Jackson |
| 5,540,224 A | 7/1996 | Buret et al. |
| 7,171,962 B1 | 2/2007 | Bloem |
| 8,220,461 B1 * | 7/2012 | Guerra et al. ............ 128/207.14 |
| 2003/0131853 A1 | 7/2003 | Wall, Jr. et al. |
| 2003/0150461 A1 | 8/2003 | Dhuper et al. |
| 2006/0130840 A1 | 6/2006 | Porat et al. |
| 2008/0295849 A1 | 12/2008 | Reynolds |
| 2008/0308108 A1 | 12/2008 | Diorio |
| 2009/0260632 A1 | 10/2009 | Abnousi et al. |

\* cited by examiner

*Primary Examiner* — Steven Douglas
(74) *Attorney, Agent, or Firm* — Richard G. Eldredge

(57) ABSTRACT

An oral airway for insertion into a mouth and pharynx of a patient to provide a breathing pathway and for cooperating with either an anesthesia breathing connector, a suction tube, or a nasal cannula. The oral airway includes a first tubular member, a second tubular member disposed within the first tubular member, and a connector configured to securely attach to both the first tubular member and the second tubular member. The connector includes a first portion in fluid communication with the first tubular member and a second portion in fluid communication with the second tubular member.

13 Claims, 9 Drawing Sheets

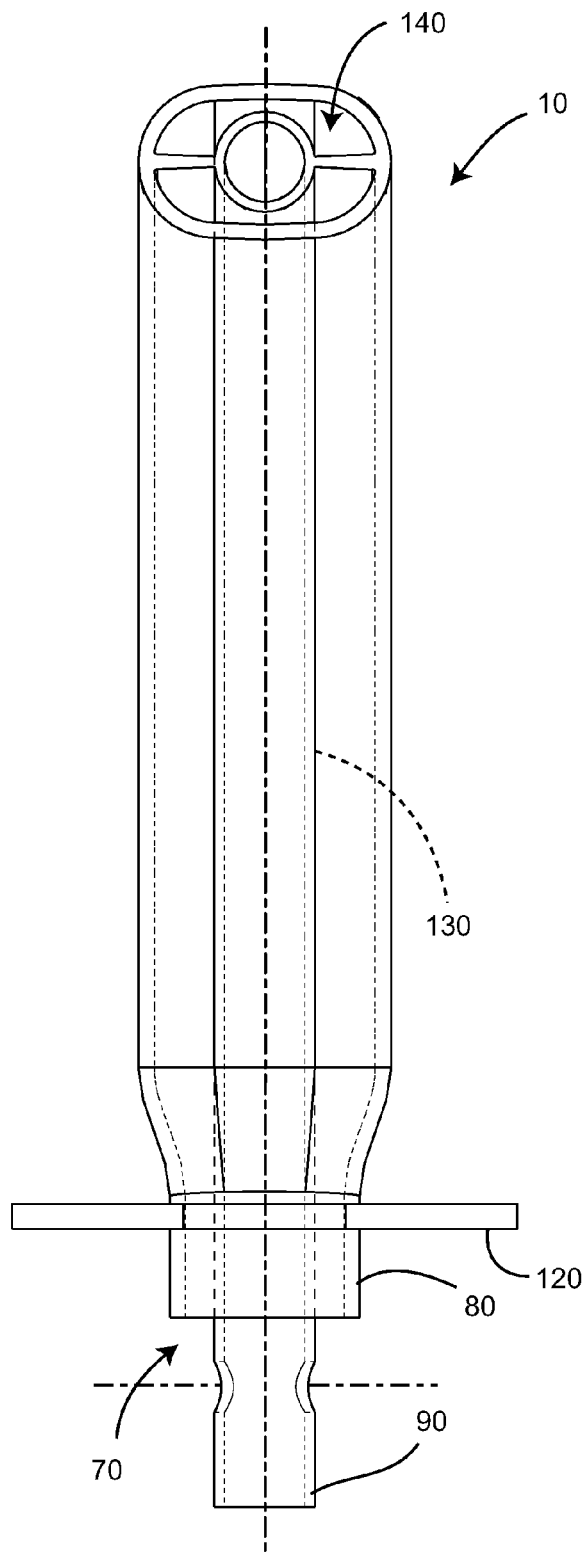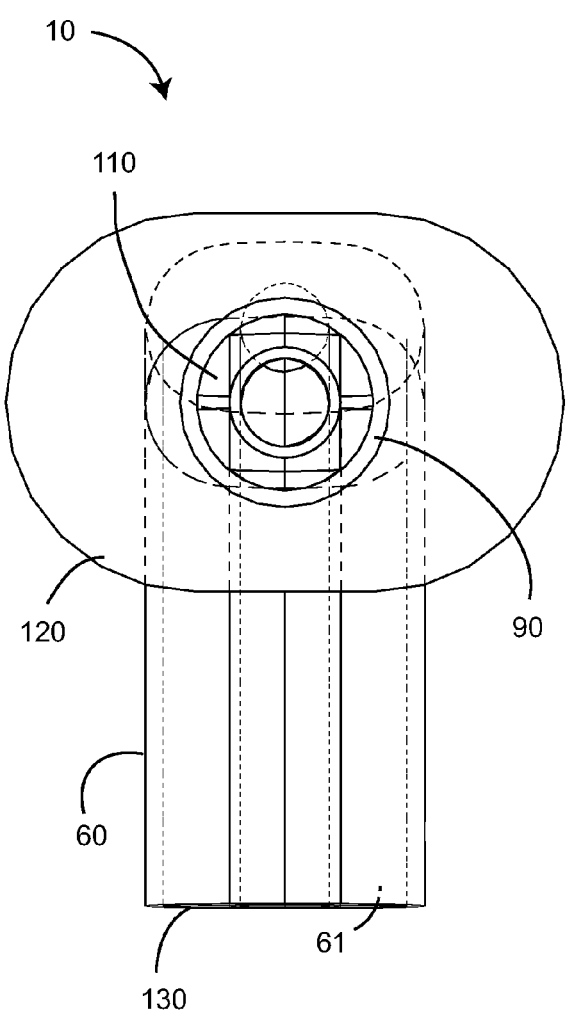
FIG. 3
FIG. 4

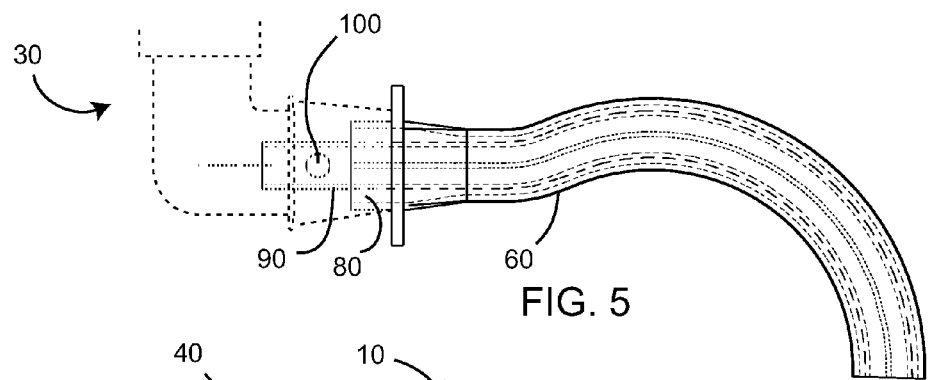
FIG. 5
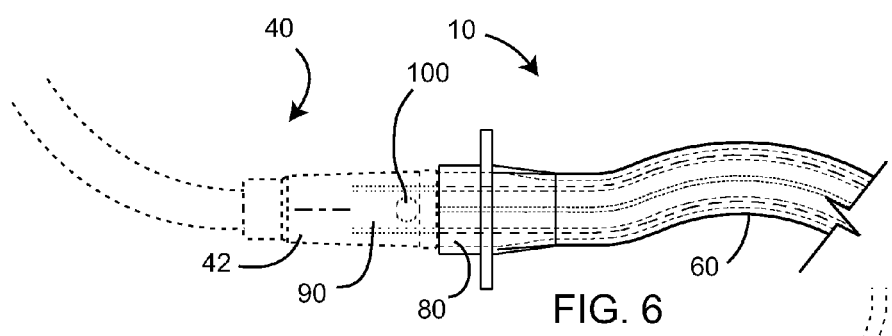
FIG. 6
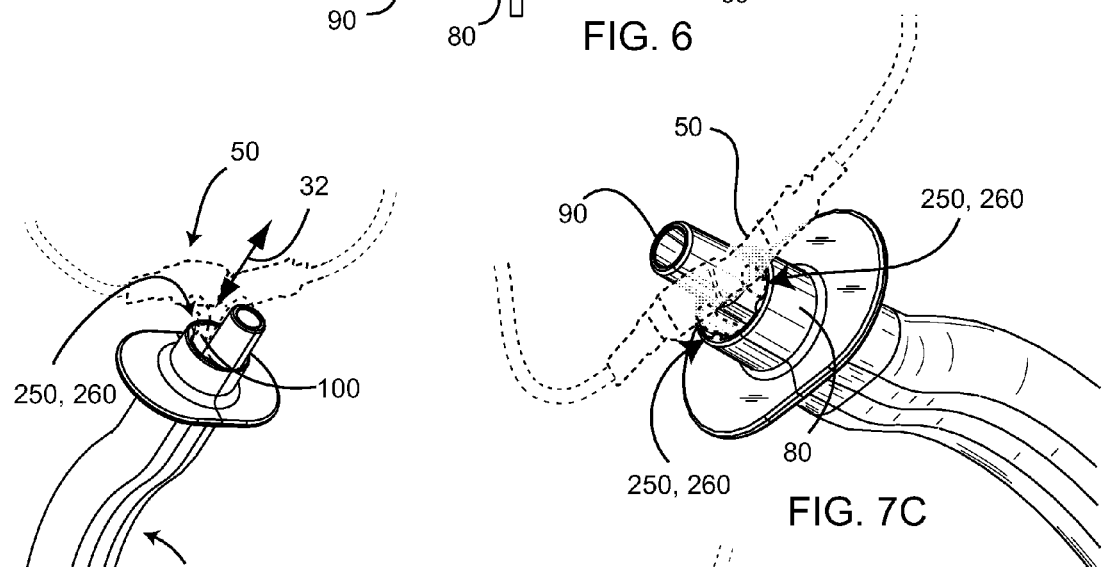
FIG. 7A
FIG. 7C
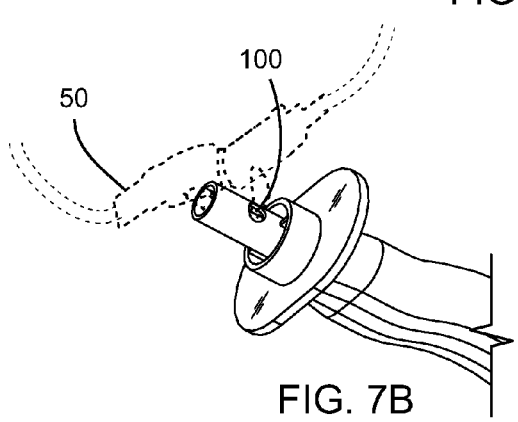
FIG. 7B

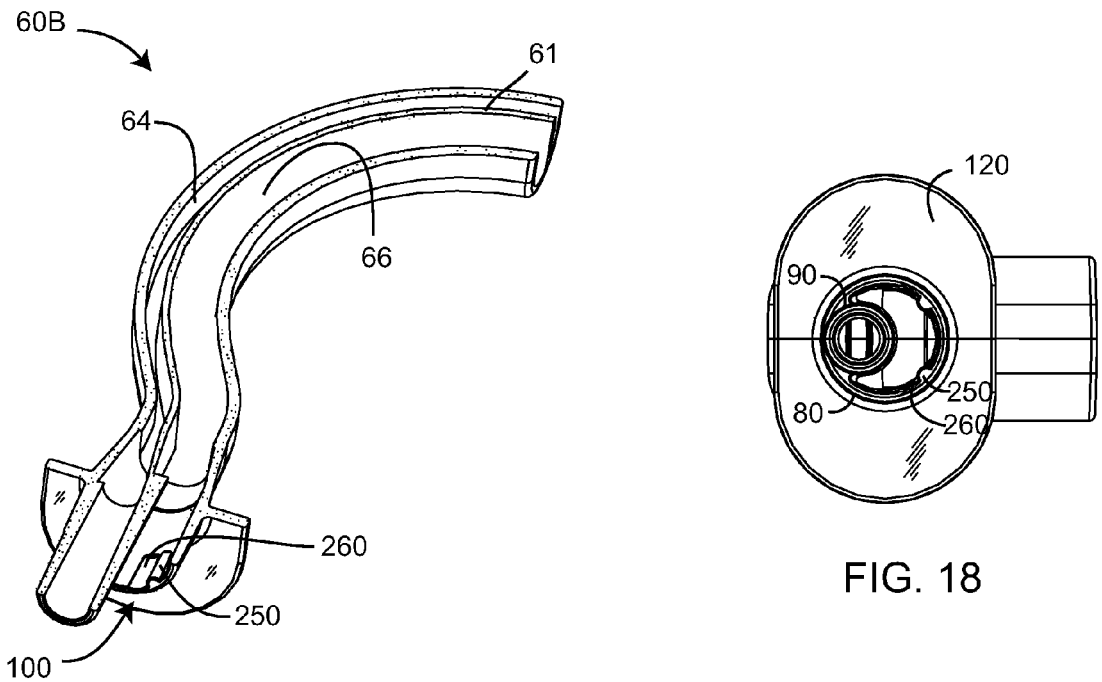
FIG. 17
FIG. 18
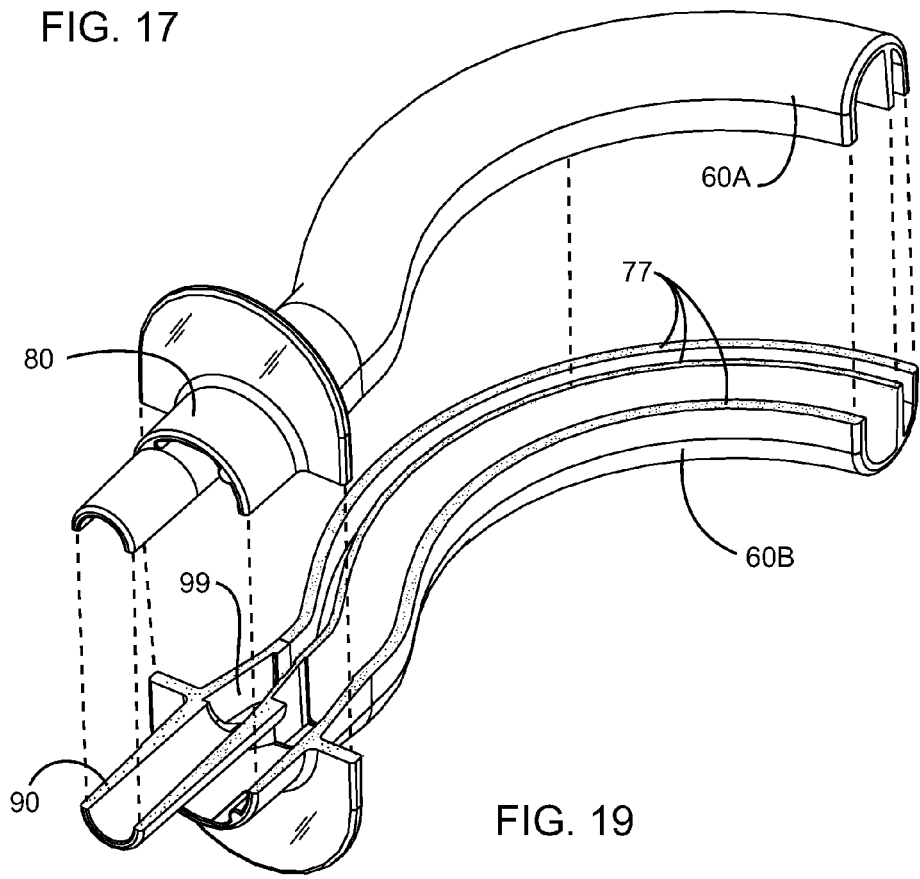
FIG. 19

ORAL AIRWAY

CROSS-REFERENCE TO RELATED APPLICATIONS

This application claims the benefit of U.S. Provisional Patent Application 61/438,465, filed on Feb. 1, 2011, and incorporated herein by reference.

STATEMENT REGARDING FEDERALLY SPONSORED RESEARCH AND DEVELOPMENT

Not Applicable.

FIELD OF THE INVENTION

This invention relates to medical devices, and more particularly to a multi-configuration oral airway.

DISCUSSION OF RELATED ART

Oral airways are known in the art, some of which allow connection to an anesthesia breathing connector, a suction tube, or a nasal cannula. However, none of the oral airways of the prior art teach the ability to connect to all three types with the same device, and without the necessity of removing the oral airway device.

Some prior art devices teach having one airway device with the ability to provide suction via the airway, such as U.S. Patent Application 2003/0131853 by Wall, Jr. et al. published on Jul. 17, 2003. However, the Wall, Jr. et al. device has the disadvantage of providing only one enclosed conduit. U.S. Pat. No. 3,756,244 to Kinnear et al. on Sep. 4, 1973 teaches a breathing aid conduit with a plurality of channels for guiding a suction catheter and keeping the other channels open. However, the Kinnear et al. device does not teach the advantage of providing completely separate enclosed suction conduits and breathing conduits. Also, neither of these devices teach the advantage of efficiently attaching nasal cannula to provide an effective third option of using readily available nasal cannula to administer oxygen via the mouth instead of the nasal passage.

Some prior art devices teach various techniques for connecting nasal cannula to a device to provide oxygen via the mouth. In particular U.S. Pat. No. 5,513,634 to Jackson on May 7, 1996 teaches a combination integral bite block airway and nasal cannula. Also, U.S. Pat. No. 7,171,962 to Bloem on Feb. 6, 2007 teaches a soft oral airway for intravenous anesthesia with two slots for a nasal cannula. And U.S. Pat. No. 5,413,095 to Weaver on May 9, 1995 teaches a mouthpiece with oxygen receiving and directing structure with two nasal cannula connectors. However, despite the development of these approaches to connecting nasal cannula, none of these approaches teach how to efficiently integrate connecting a nasal cannula with an oral airway device having both a completely separate suction conduit and a breathing conduit.

Therefore, there is a need for an oral airway device that connects to either an anesthesia breathing connector, suction tube, or nasal cannula, without necessitating the removal of the device from the patient. The present invention accomplishes these objectives.

SUMMARY OF THE INVENTION

The present device is an oral airway for insertion into the mouth and pharynx of a patient. The oral airway is adapted to connect to an anesthesia breathing connector, a suction tube, or a nasal cannula, interchangeably as needed, without necessitating the removal of the oral airway from the patient.

An arcuate hollow tubular member has a proximal end and a distal end adapted for inserting into the mouth and pharynx of the patient. A connector is fixed with the proximal end of the tubular member and includes a first portion that is adapted for fixing with the anesthesia breathing connector. A second portion of the connector is adapted for receiving the suction tube. At least one aperture is included in the second portion that is adapted for receiving a portion of the nasal cannula.

When the anesthesia breathing connector is connected to the first portion of the connector, the at least one aperture is sealed from the ambient atmosphere. Further, the anesthesia breathing connector is in fluid communication with the tubular member via at least one open gap formed between the first and second portions of the connector. A mouth guard extends outwardly from the connector.

In one embodiment of the invention, the tubular member further includes a suction tube guide therein spanning substantially the length of the tubular member between the distal end thereof and the connector. The suction tube guide may be slidably positionable within the tubular member between a retracted position wherein the suction tube guide is substantially contained within the tubular member and an extended position wherein at least a portion of the suction tube guide extends past the distal end of the tubular member.

The present device is an oral airway that connects to an anesthesia breathing connector, a suction tube, or a nasal cannula, without necessitating the removal of the device from the patient. Further, the present invention, in one embodiment, allows for pinpoint depth adjustment of the suction tube. Using institutions will enjoy cost savings due to feature overlap with Yankauer suction tips, mask straps, and Laryngeal Mask Airways (LMAs), allowing in a percentage of procedures, discontinuance of use of some of these devices. Other features and advantages of the present invention will become apparent from the following more detailed description, taken in conjunction with the accompanying drawings, which illustrate, by way of example, the principles of the invention.

DESCRIPTION OF THE DRAWINGS

FIG. 3 is a bottom plan view of the device illustrated in FIG. 1;

FIG. 4 is a front elevational view of the device illustrated in FIG. 1;

FIG. 5 is a side elevational view of the device shown in FIG. 1, illustrated as used with an anesthesia breathing connector;

FIG. 6 is a side elevational view of the device shown in FIG. 1, illustrated as used with a suction tube;

FIG. 7A is a perspective view of an alternate embodiment of the invention, illustrated as used with a nasal cannula;

FIG. 7B is a partial perspective view of the device shown in FIG. 1, illustrated as used with a nasal cannula;

FIG. 7C is a partial perspective view of an alternate embodiment of the invention, illustrated as used with a nasal cannula;

FIG. 17 is a partial view of one half of the tubular element of the device illustrated in FIG. 15;

FIG. 18 is a front elevational view of the device illustrated in FIG. 15;

FIG. 19 is an exploded perspective view of the device illustrated in FIG. 15;

DETAILED DESCRIPTION OF THE PREFERRED EMBODIMENT

Illustrative embodiments of the invention are described below. The following explanation provides specific details for a thorough understanding of and enabling description for these embodiments. One skilled in the art will understand that the invention may be practiced without such details. In other instances, well-known structures and functions have not been shown or described in detail to avoid unnecessarily obscuring the description of the embodiments.

Unless the context clearly requires otherwise, throughout the description and the claims, the words "comprise," "comprising," and the like are to be construed in an inclusive sense as opposed to an exclusive or exhaustive sense; that is to say, in the sense of "including, but not limited to." Words using the singular or plural number also include the plural or singular number respectively. Additionally, the words "herein," "above," "below" and words of similar import, when used in this application, shall refer to this application as a whole and not to any particular portions of this application. When the claims use the word "or" in reference to a list of two or more items, that word covers all of the following interpretations of the word: any of the items in the list, all of the items in the list and any combination of the items in the list.

Figure 1:
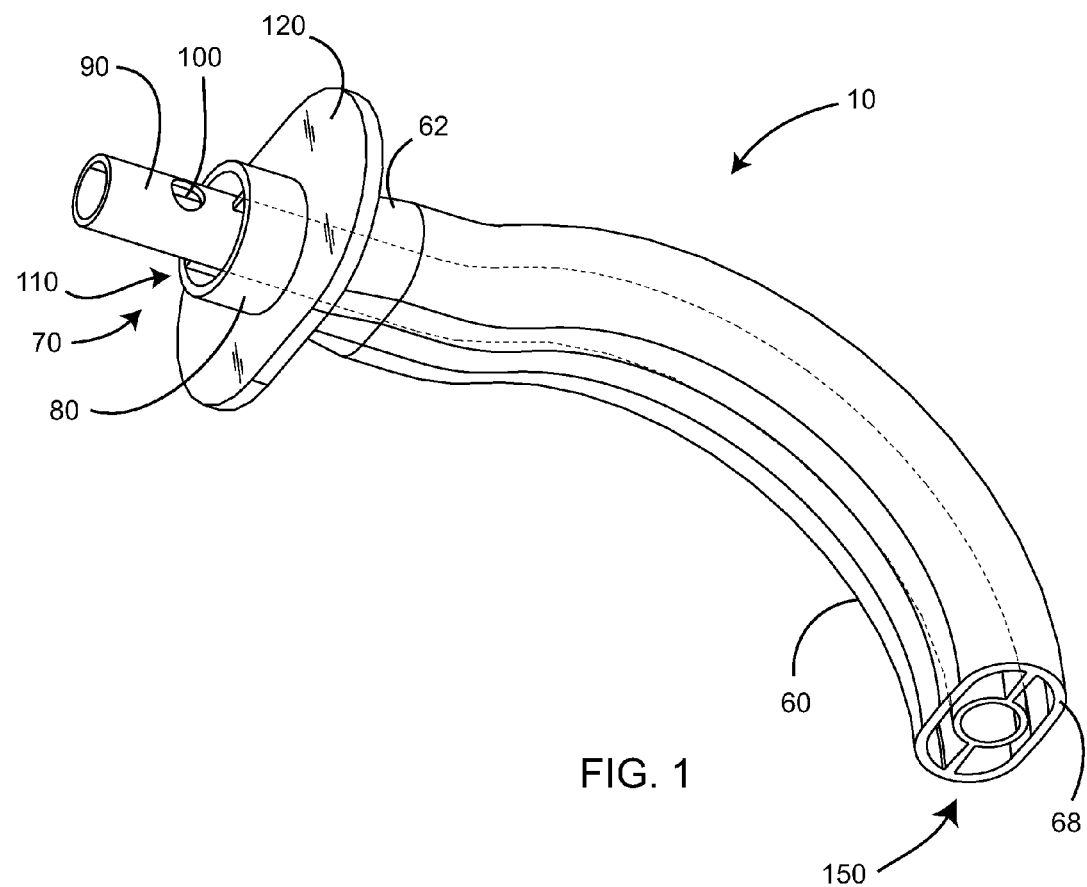
FIG. 1 is a perspective view of one embodiment of the invention.
Figure 2:
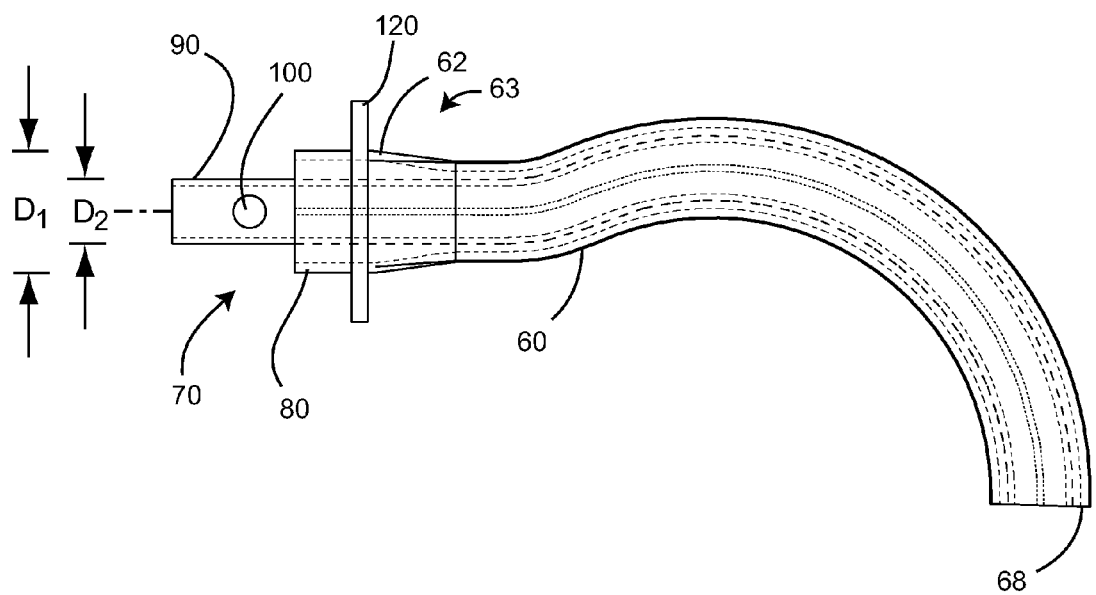
FIG. 2 is a side elevational view of the device illustrated in FIG. 1.

With respect to the drawings, FIGS. 1 and 2 illustrate an oral airway 10 for insertion into the mouth and pharynx of a patient (not shown), thereby providing a breathing pathway 32 (FIG. 7A). The oral airway 10 is adapted to connect to either an anesthesia breathing connector 30 (FIG. 5), a suction tube 40 (FIG. 6), or a nasal cannula 50 (FIGS. 7A-7C), interchangeably as needed, without necessitating the removal of the oral airway 10 from the patient.

In FIG. 1, an arcuate hollow tubular member 60 has a proximal end 62 and a distal end 68. The tubular member 60 is adapted for inserting the distal end 68 first into the mouth and pharynx of the patient. Preferably the tubular member 60 is made from a non-toxic, semi-rigid plastic material.

In FIGS. 1-3, a connector 70 is fixed with the proximal end 62 of the tubular member 60 and includes a first portion 80 having a first diameter $D_1$ (FIG. 2). The first portion 80 is adapted for fixing with the anesthesia breathing connector 30 (FIG. 5). A second portion 90 of the connector 70 has a second diameter $D_2$ (FIG. 2) that is smaller than the first diameter $D_1$. The second portion 90 is adapted for receiving the suction tube 40 (FIG. 6) which may include a suction connector 42. Further, the anesthesia breathing connector 30 is in fluid communication with the tubular member 60 via at least one open gap 110 (FIGS. 1 and 4) formed between the first and second portions 80,90 of the connector 70. Preferably the connector 70 is made from a rigid, non-toxic plastic material. It should be noted that diameters $D_1$ and $D_2$ may be the proximal end diameters of connector 70 first and second portions 80,90 wherein those connector portions 80,90 are conical frustums such that anesthesia breathing connector 30 and suction connector 42 respectively adequately seal when affixed thereto.

The first and second portions 80,90 of the connector 70 are adapted to receive and retain therebetween a portion of the nasal cannula 50 (FIGS. 7A, 7B. and 10-17). In at least one embodiment, at least one protuberance 250 (FIGS. 7A, 7C, 15-21) between the first and second portions 80,90 is included and adapted for receiving and retaining therebetween a portion of the nasal cannula 50. Further, a groove 260 (FIGS. 7A, 7C, 15-21) may be included adjacent to each protuberance 250 for further facilitating the retention of the nasal cannula 50 between the first and second portions 80,90 of the connector 70.

In an alternate embodiment, at least one aperture 100 (FIGS. 1--6, 7B, 8 and 9) is included in the second portion 90 that is adapted for receiving a portion of the nasal cannula 50 (FIG. 7B). In such an embodiment, when the anesthesia breathing connector 30 is connected to the first portion 80 of the connector 70, the at least one aperture 100 is sealed from the ambient atmosphere, as illustrated in FIG. 5.

In FIGS. 1 and 2, a mouth guard 120 extends outwardly from the connector 70 $_1$. The mouth guard 120 is preferably integrally formed with the connector 70, such as in a plastic injection molding process. Alternately, the mouth guard 120 may include a central aperture therein (not shown), whereby the mouth guard 120 being selectively fixable against the connector 70 by inserting the distal end 68 of the tubular member 60 to the central aperture of the mouth guard 120 and sliding the mouth guard 120 up the tubular member 60 to the connector 70. In yet another alternate embodiment, the mouth guard 120 includes a U-shaped slot (not shown) adapted for selectively removable attachment around an outer surface of the connector 70. The mouth guard 120 may further include mask strap prongs (not shown) at side edges thereof, whereby an elastic strap (not shown) may be fixed to each mask strap prong and secured around the patient's head to retain the oral airway 10 in place on the patient. Preferably the mouth guard 120 is made from a rigid, non-toxic plastic material. The oral airway 10 may further include an integral bite guard region 63 on the distal side of the mouth guard 120 at the proximal end 62 of the tubular member 60 wherein the transition from the mouth guard 120 to the tubular member 60 includes increased wall thickness (FIG. 2).

Figure 8:
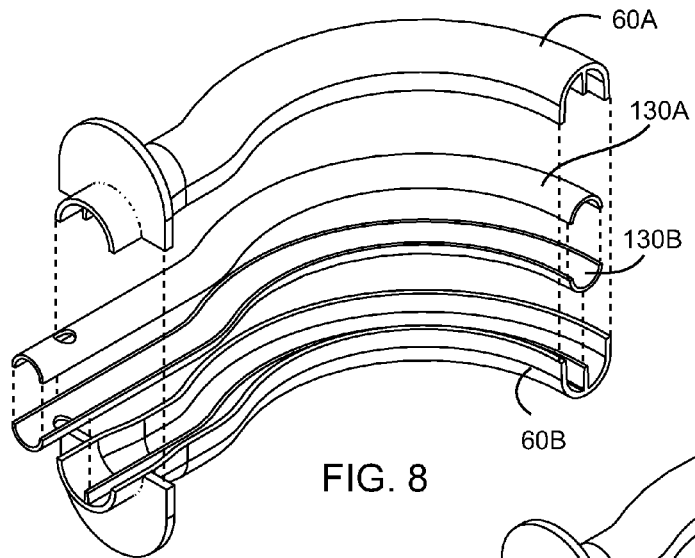
FIG. 8 is an exploded perspective view of an alternate embodiment of the invention.
Figure 9:
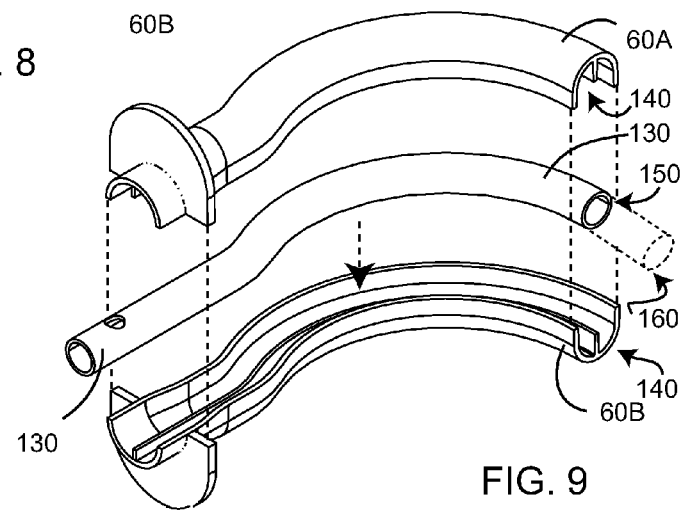
FIG. 9 is an exploded perspective view of another alternate embodiment of the invention.

In one embodiment of the invention, the tubular member 60 further includes a suction tube guide 130 therein spanning substantially the length of the tubular member 60 between the distal end 68 thereof and the connector 70 (FIGS. 8-9). The suction tube guide 130 may be a length of flexible transparent tubing, for example (FIG. 9). A gap 140 between the suction tube guide 130 and the tubular member 60 allows air flow therebetween (FIGS. 3 and 9).

In one embodiment in FIG. 9, the suction tube guide 130 is slidably positionable within the tubular member 60 between a retracted position 150 wherein the suction tube guide 130 is substantially contained within the tubular member 60 and an extended position 160 wherein at least a portion of the suction tube guide 130 extends past the distal end 68 of the tubular member 60. In such an embodiment, the suction tube guide 130 may further include at least one locking tab (not shown) at a proximal end thereof, and an internal wall of the tubular member 60 may include at least one locking tab groove (not shown) for capturing the locking tab between a locked position with the suction tube guide 130 in the retracted position 150, and an unlocked position wherein the suction tube guide 130 may be moved away from the retracted position 150 towards the extended position 160.

As illustrated in FIG. 8, the suction tube guide 130 may be formed as two halves 130A,130B that are ultrasonically welded, solvent bonded, or otherwise mutually fixed together. The tubular member 60 may also be formed as two halves 60A,60B and ultrasonically welded, solvent bonded, or otherwise mutually fixed together around the suction tube guide 130 (FIG. 8). The suction tube guide 130 may alternately be a length of tubing that is captured between two halves 60A, 60B of the tubular member 60 (FIG. 9) which is then ultrasonically welded or otherwise fixed therearound.

Alternately, in an alternate embodiment (not shown), the suction tube guide 130 and the first portion 80 of the connector 70 are mutually fixed together and both slidably positionable together within the tubular member 60 between the retracted position, wherein the suction tube guide 130 is substantially contained within the tubular member 60, and the extended position, wherein at least a portion of the suction tube guide 130 extends past the distal end 68 of the tubular member 60. In such an embodiment, the first portion 80 of the connector 70 may include at least one of the locking tabs, and wherein the second portion 90 of the connector 70 may include at least one of the locking tab grooves for capturing the locking tab between the locked position and the unlocked position. As such, the first portion 80 of the connector 70 and the suction tube guide 130 may be moved together away from the refracted position towards the extend position.

Figure 10:
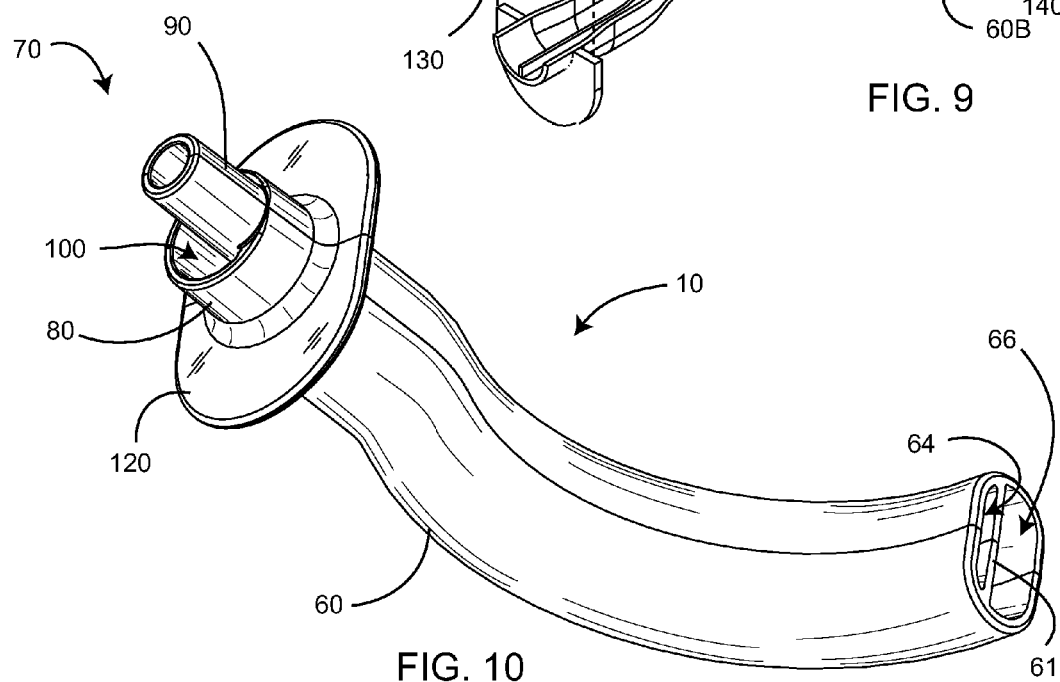
FIG. 10 is a perspective view of the embodiment illustrated in FIG. 7A.
Figure 11:
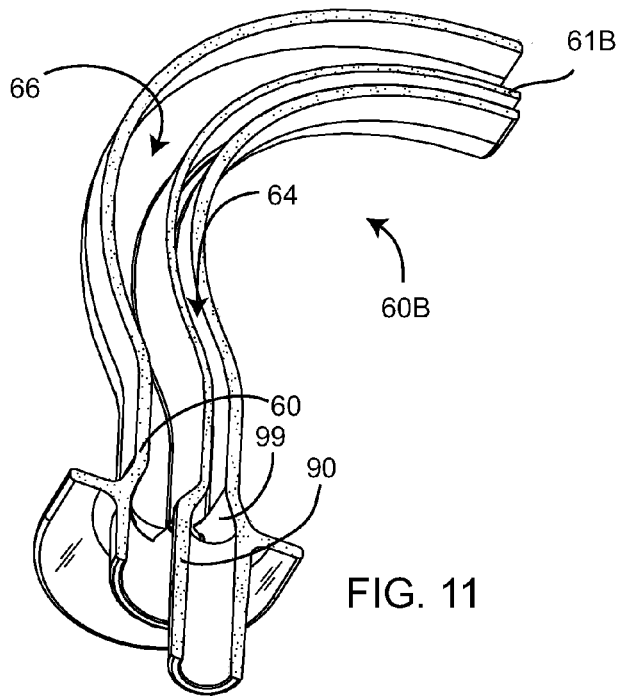
FIG. 11 is a perspective view of one half of the tubular element of the device illustrated in FIG. 10.
Figure 12:
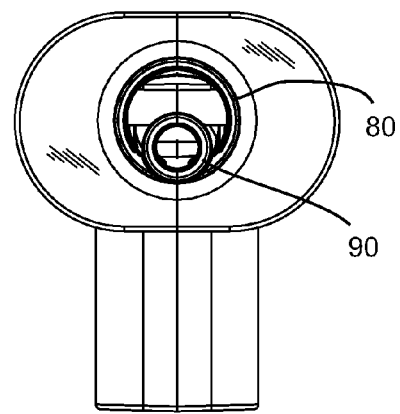
FIG. 12 is a front elevational view of the device illustrated in FIG. 10.
Figure 13:
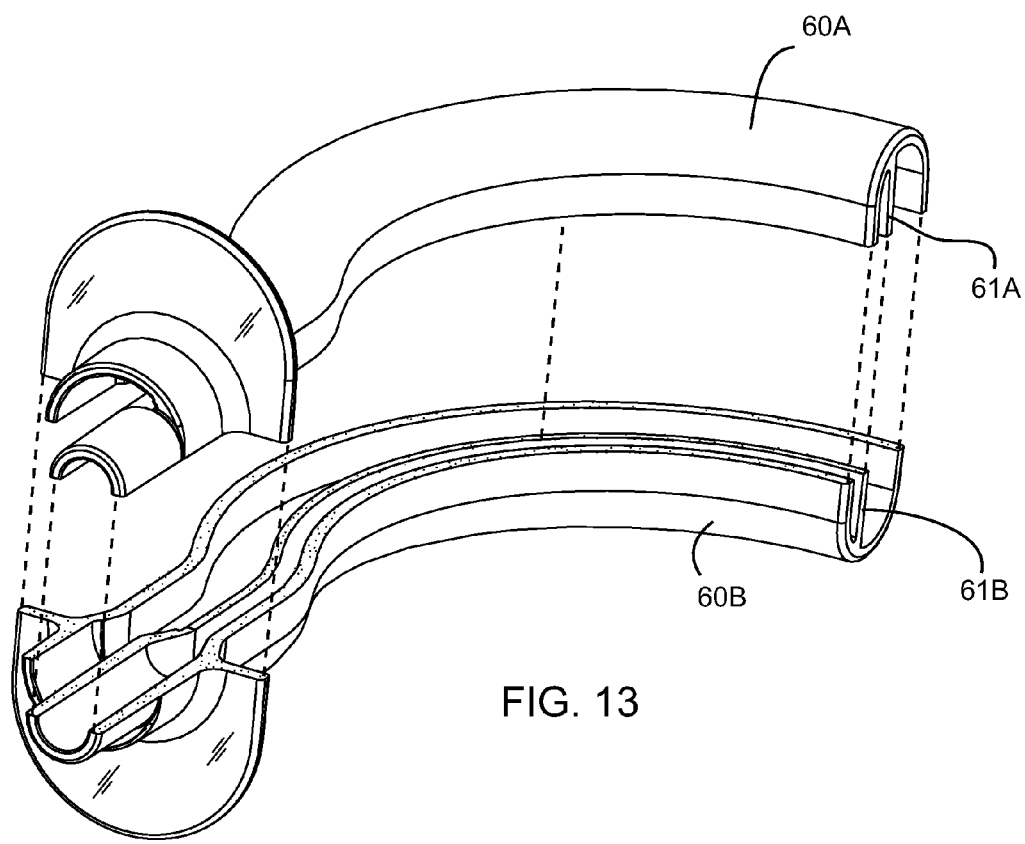
FIG. 13 is an exploded perspective view of the device illustrated in FIG. 10.
Figure 14:
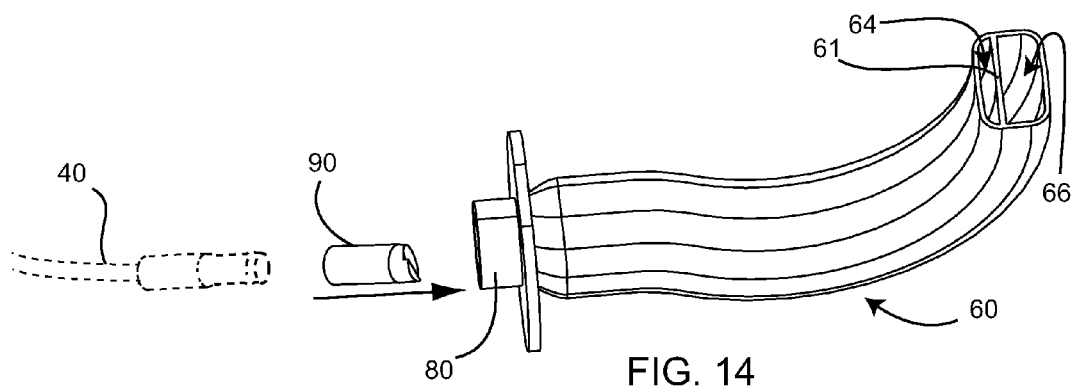
FIG. 14 is a perspective view of yet another embodiment of the invention having a suction conduit and a breathing conduit.
Figure 15:
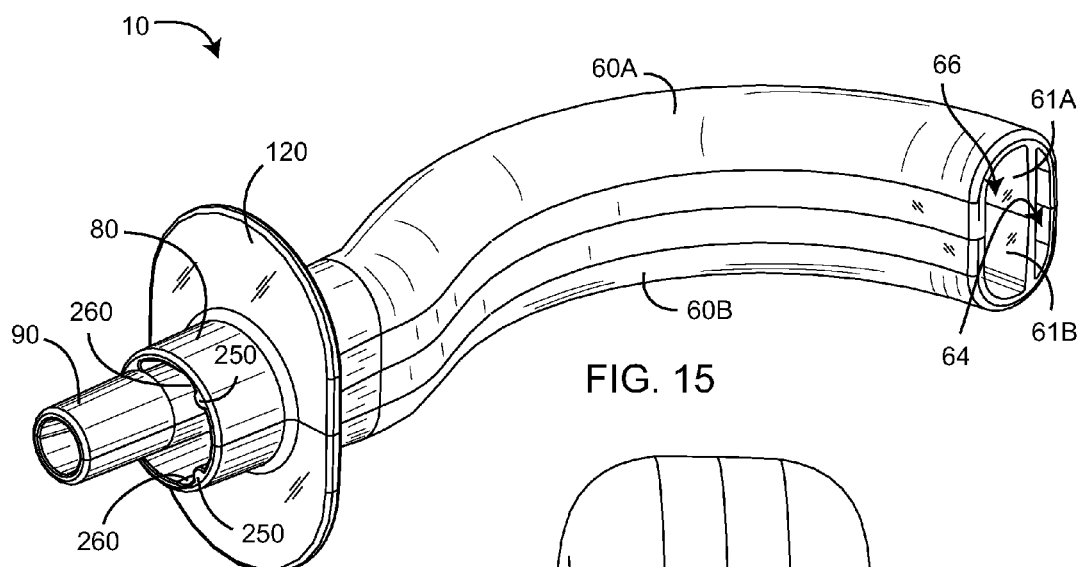
FIG. 15 is a perspective view of an alternate embodiment of the invention.
Figure 16:
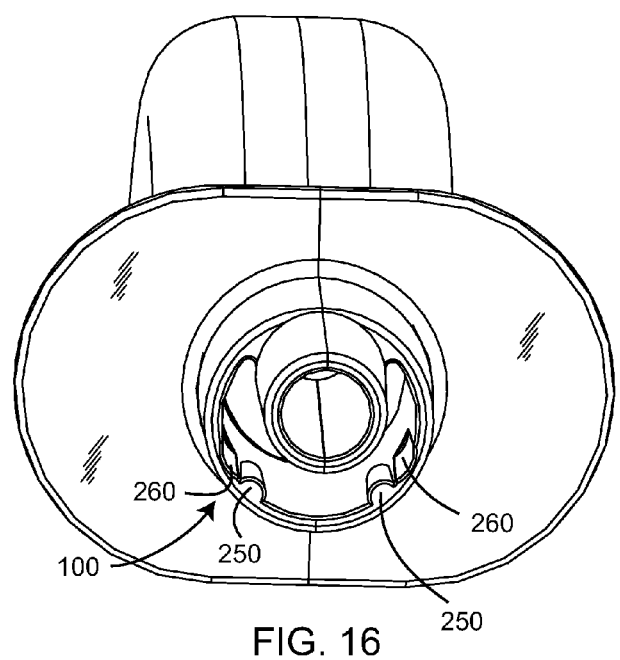
FIG. 16 is a front perspective view of the device illustrated in FIG. 15.

In one alternate preferred embodiment (FIGS. 10-13), the oral airway 10 is formed as two halves that divides the tubular member 60 into two halves 60A,60B that are fixed together with ultrasonic welding, solvent bonded, or otherwise mutually fixed together. Each half 60A,60B of the tubular member 60 further including one half 61A,61B of a conduit separator 61 (FIGS. 10-11 and 13) that spans the length of the tubular member 60 and bifurcates the tubular member 60 into a suction conduit 64 and a breathing conduit 66. In FIG. 11, the second portion 90 of the connector 70 may include a funnel 99 that is in fluid communication with only the suction conduit 64. As such, in FIG. 14, when the suction tube 40 is fixed within the second portion 90 of the connector 70, only the suction conduit 64 is in fluid communication therewith, and not the breathing conduit 66. Such an embodiment may be formed by fixing together each half 60A,60B of the tubular member 60, and then fixing the second portion 90 of the connector 70 into the first portion 80 of the connector 70, such that the funnel 99 is aligned with the suction conduit 64, with a suitable cement adhesive or ultrasonic welding method, as illustrated in FIG. 14. In an alternate preferred embodiment, the location of the suction conduit 64 and the breathing conduit 66 may be reversed, as illustrated in FIGS. 15-19, with the location of the second portion 90 of the connector 70 reversed accordingly. In one situation, when the patient is lying face up, it is preferable to locate the suction conduit towards a back side of a patient's throat where fluid may be gathering. In another situation, when the patient is lying face down, it is preferable to locate the suction conduit towards a front side of a patient's throat where fluid may be gathering.

Figure 20:
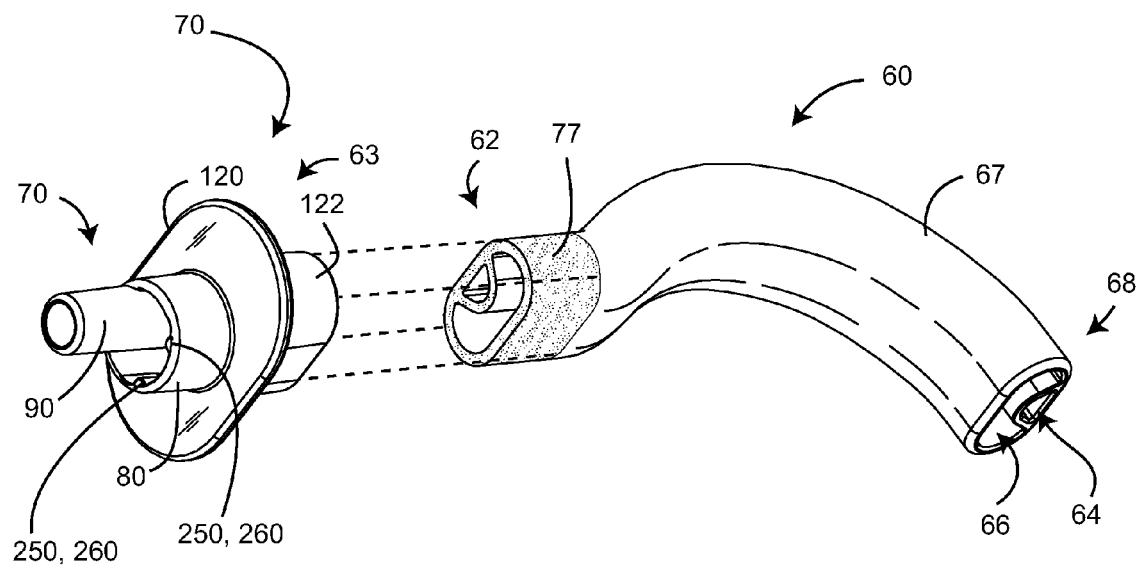
FIG. 20 is an exploded front perspective view of yet another embodiment of the invention, illustrating multi-lumen extruded tubing.
Figure 21:
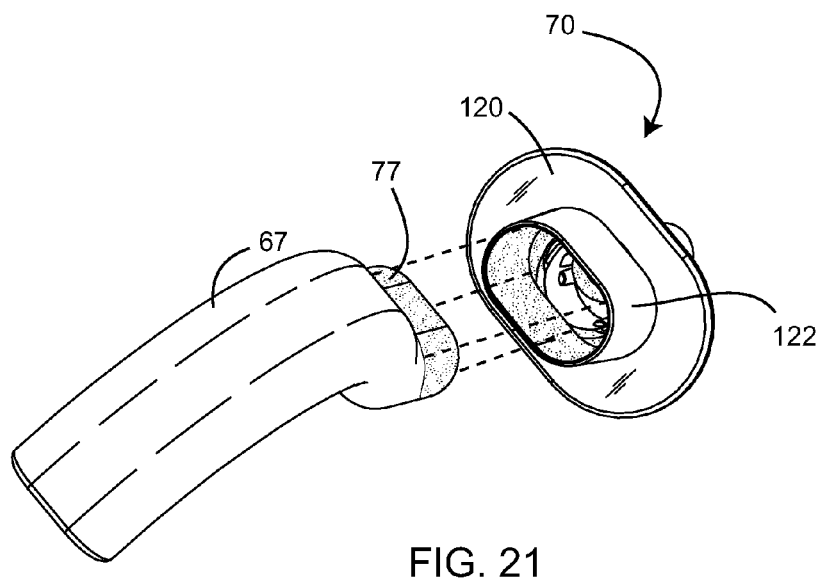
FIG. 21 is an exploded back perspective view of the device illustrated in FIG. 20.

FIGS. 20 and 21 illustrate yet another preferred embodiment wherein the tubular member 60 is an arcuate multi-lumen extruded tube 67 and connector 70 includes a tube socket 122 adapted for receiving the proximal end 62 of the multi-lumen extruded tube 67. In one embodiment, the connector 70 and tubular member 60 are fixed together with a solvent bonding process, in particular using a solvent bond 77. In another embodiment, the connector 70 and the multi-lumen extruded tube 67 are fixed together with a permanent adhesive, or ultrasonic welding, or the like. The tube socket 122 may further serve as a bite guard 63.

Figure 22:
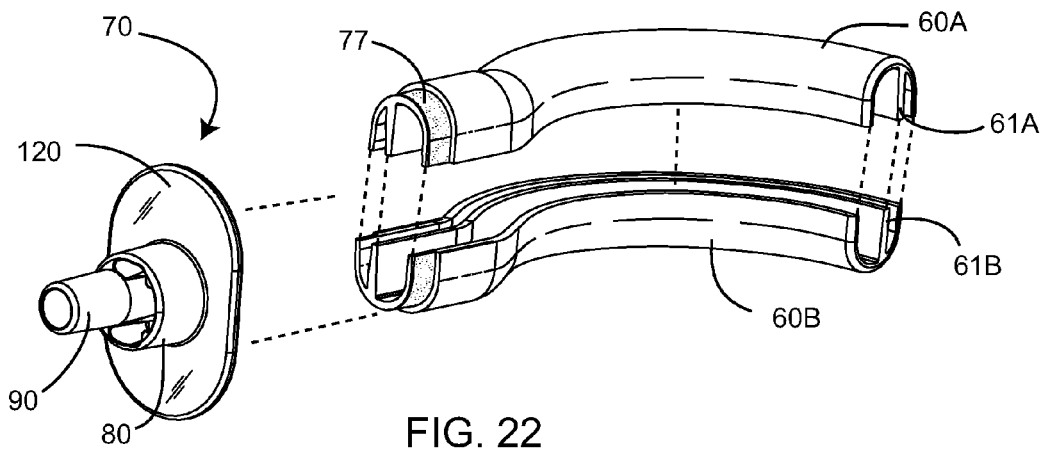
FIG. 22 is an exploded perspective view of yet another embodiment of the invention.
Figure 23:
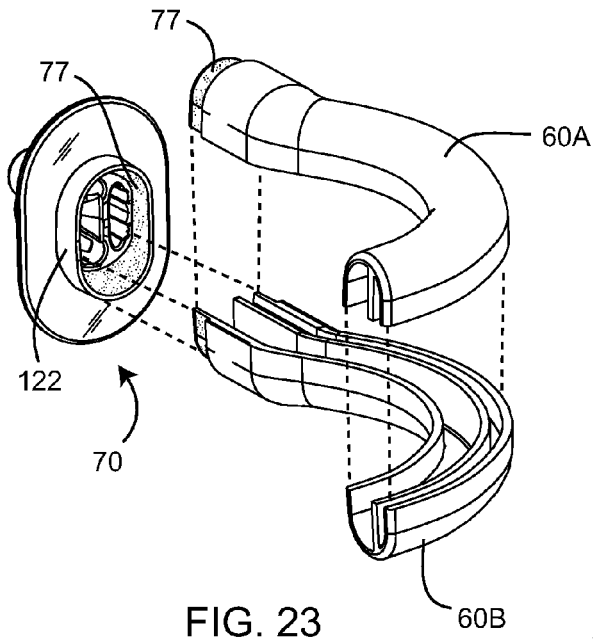
FIG. 23 is an alternate exploded perspective view of the embodiment of FIG. 22.
Figure 24:
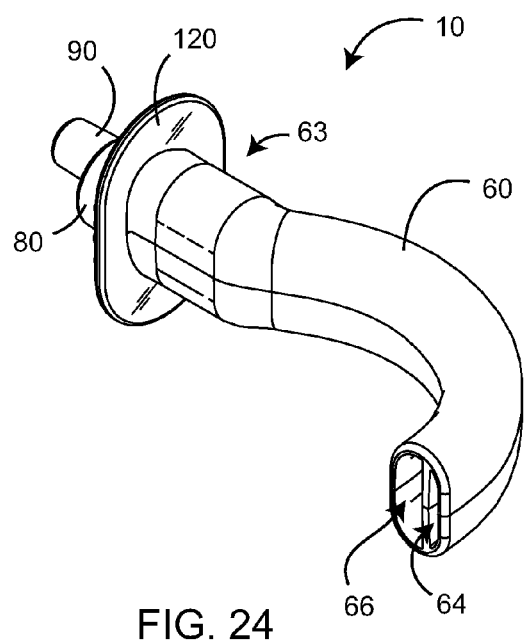
FIG. 24 is a perspective view of the embodiment of FIG. 22 as assembled.

Alternatively, an oral airway (FIGS. 22-24) comprises three injection-molded parts, namely the connector 70 with the socket 122, and tubular member 60 formed as two halves 60A,60B. One advantage of such an embodiment is that the injection molds (not shown) for such parts may be relatively simple, without any side pulls or the like.

While a particular form of the invention has been illustrated and described, it will be apparent that various modifications can be made without departing from the spirit and scope of the invention. For example, three types of connectors are illustrated as cooperating with the oral airway of the present invention, but other types of conduit connectors may also be adapted for use therewith. Accordingly, it is not intended that the invention be limited, except as by the appended claims.

Particular terminology used when describing certain features or aspects of the invention should not be taken to imply that the terminology is being redefined herein to be restricted to any specific characteristics, features, or aspects of the invention with which that terminology is associated. In general, the terms used in the following claims should not be construed to limit the invention to the specific embodiments disclosed in the specification, unless the above Detailed Description section explicity defines such terms. Accordingly, the actual scope of the invention encompasses not only the disclosed embodiments, but also all equivalent ways of practicing or implementing the invention.

The above detailed description of the embodiments of the invention is not intended to be exhaustive or to limit the invention to the precise form disclosed above or to the particular field of usage mentioned in this disclosure. While specific embodiments of, and examples for, the invention are described above for illustrative purposes, various equivalent modifications are possible within the scope of the invention, as those skilled in the relevant art will recognize. Also, the teachings of the invention provided herein can be applied to other systems, not necessarily the system described above. The elements and acts of the various embodiments described above can be combined to provide further embodiments.

All of the above patents and applications and other references, including any that may be listed in accompanying filing papers, are incorporated herein by reference. Aspects of the invention can be modified, if necessary, to employ the systems, functions, and concepts of the various references described above to provide yet further embodiments of the invention.

Changes can be made to the invention in light of the above "Detailed Description." While the above description details certain embodiments of the invention and describes the best mode contemplated, no matter how detailed the above appears in text, the invention can be practiced in many ways. Therefore, implementation details may vary considerably while still being encompassed by the invention disclosed herein. As noted above, particular terminology used when describing certain features or aspects of the invention should not be taken to imply that the terminology is being redefined herein to be restricted to any specific characteristics, features, or aspects of the invention with which that terminology is associated.

While certain aspects of the invention are presented below in certain claim forms, the inventor contemplates the various aspects of the invention in any number of claim forms. Accordingly, the inventor reserves the right to add additional claims after filing the application to pursue such additional claim forms for other aspects of the invention.

What is claimed is:

1. An oral airway for insertion into a mouth and pharynx of a patient to provide a breathing pathway and for cooperating with either an anesthesia breathing connector, a suction tube, or a nasal cannula, the oral airway comprising:
   a first tubular member;
   a second tubular member disposed within the first tubular member; and
   a connector configured to securely attach to both the first tubular member and the second tubular member, the connector having:
      a first portion in fluid communication with the first tubular member; and
      a second portion in fluid communication with the second tubular member;
   wherein either the anesthesia breathing connector, the suction tube, or the nasal cannula is utilized on the patient without necessitating the removal of the oral airway from the mouth and pharynx.

2. The oral airway of claim 1, wherein the second portion attaches to either the the anesthesia breathing connector, the suction tube, or the nasal cannula.

3. The oral airway of claim 1, wherein the first tubular member and the second tubular member are fluidly separable.

4. The oral airway of claim 1, wherein the second tubular member extends the length of the first tubular member.

5. The oral airway of claim 1, further comprising:
   a mouth guard extending outwardly from an outer surface of the connector.

6. The oral airway of claim 5, wherein the mouth guard is integrally formed with the connector.

7. The oral airway of claim 1, the second portion of the connector comprises:
   an aperture configured to receive a portion of the nasal cannula.

8. The oral airway of claim 7, wherein the aperture is a hole that extends through a wall thickness of the second portion to provide fluid passage between the nasal cannula and the second tubular member.

9. The oral airway of claim 1, wherein the connector removably attaches to the first tubular member and second tubular member.

10. The oral airway of claim 1, wherein the connector is integrally formed with the first tubular member and the second tubular member.

11. The oral airway of claim 1, wherein the second portion removably attaches to the connector.

12. The oral airway of claim 1, the connector further comprising:
   a protuberance for further facilitating the retention of the nasal cannula.

13. The oral airway of claim 1, wherein the second tubular member slidingly engages with the first tubular member between a retracted position and an extended position.

* * * * *